United States Patent [19]

Wooten et al.

[11] Patent Number: 4,841,957
[45] Date of Patent: Jun. 27, 1989

[54] BRACE FOR TREATING AND RELIEVING POSTERIOR HEEL PAIN

[76] Inventors: Beven P. Wooten, 305 Lindenhurst Dr., Apt. #2092, Lexington, Ky. 40509; Tim L. Uhl, 3501 Pimlico Pkwy. #6, Lexington, Ky. 40502

[21] Appl. No.: 172,765

[22] Filed: Mar. 28, 1988

[51] Int. Cl.$^4$ .............................. A61F 5/30; A61F 5/00
[52] U.S. Cl. ................................... 128/80 H; 128/166; 128/882; 128/581
[58] Field of Search ...................... 128/80, 80 A, 80 B, 128/80 E, 80 G, 80 H, 80 J, 80 D, 80 DB, 581, 614, 623, 166, 149, 153, 166.5

[56] References Cited

U.S. PATENT DOCUMENTS

| | | | |
|---|---|---|---|
| 592,040 | 10/1897 | Allen | 128/153 |
| 958,199 | 5/1910 | Word | 128/153 |
| 2,926,661 | 3/1960 | Hipps | 128/80 D |
| 3,506,000 | 4/1970 | Baker | 128/166 |
| 3,670,725 | 6/1972 | Gaylord, Jr. | 128/149 |
| 4,133,311 | 1/1979 | Karczewski | 128/80 H |
| 4,287,884 | 9/1981 | Applegate | 128/80 C |
| 4,325,380 | 4/1982 | Malkin | 128/614 |
| 4,495,942 | 1/1985 | Palumbo | 128/80 H |
| 4,688,562 | 8/1987 | Buchan et al. | 128/153 |

OTHER PUBLICATIONS

Lynco Biomechanical Sports/Comfort/Conform Support Systems.
Apex Foot Health Industries, Inc. Catalog—p. 11.
Osgood Schlatter Strap.

*Primary Examiner*—Edgar S. Burr
*Assistant Examiner*—Kimberly L. Asher
*Attorney, Agent, or Firm*—King & Schickli

[57] ABSTRACT

A brace is provided for treating inflamed tissue and relieving posterior heel pain. The brace includes a mounting member having a foot receiving sleeve and an upper body portion for fastening around the ankle. A heel receiving opening and an ankle face opening provided in the mounting member allows full freedom of ankle movement while serving to minimize any movement of the brace relative to the ankle and heel. A treatment pad is fastened to the upper body portion of the mounting member above the heel opening. The treatment pad is substantially U-shaped including two substantially parallel arms and a base portion joining the arms. The pad is selectively positionable so as to be adapted to provide a cushion to reduce pressure on the inflamed tissue of the heel. When inverted, the pad serves to provide a counterforce across the Achilles tendon that reduces longitudinal stress.

12 Claims, 2 Drawing Sheets

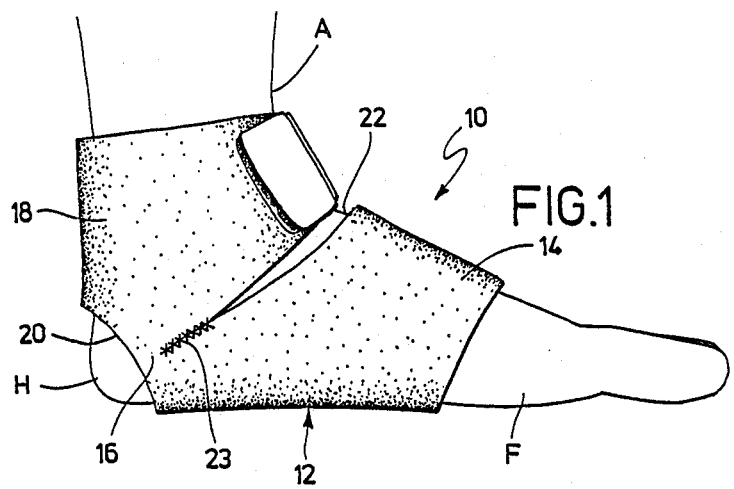
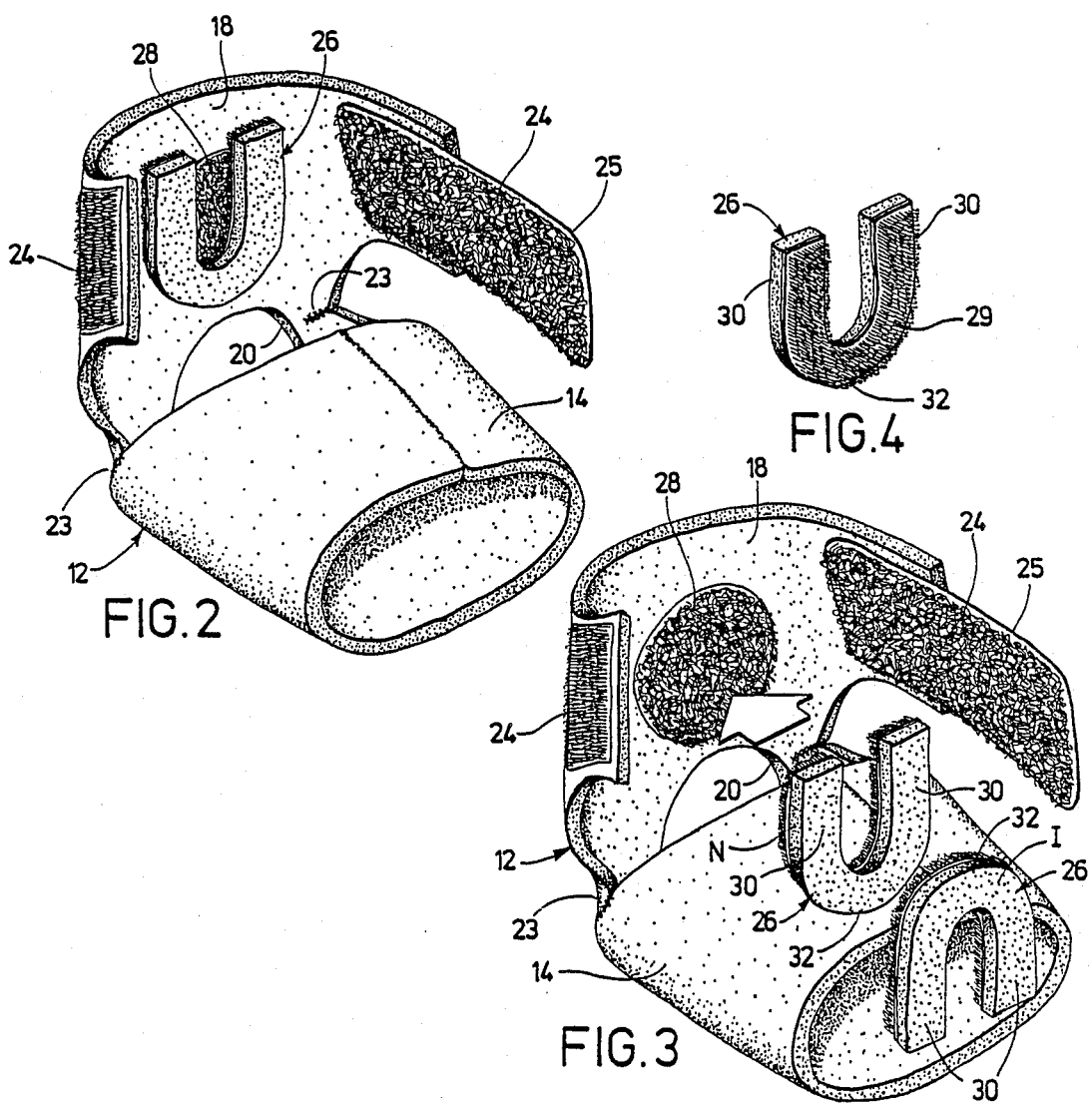

BRACE FOR TREATING AND RELIEVING POSTERIOR HEEL PAIN

TECHNICAL FIELD

The present invention relates generally to the medical field and, more particularly, to a prosthetic device in the form of a brace specially adapted for treating and relieving posterior heel pain.

BACKGROUND OF THE INVENTION

Posterior heel pain is a fairly common affliction affecting a large number of individuals at least at some time in their lives to varying degrees. There are three accepted common causes of posterior heel pain known to the medical profession as (1) Haglund syndrome (pump bump deformity), (2) Achilles tendonitis and (3) Sever's disease.

Haglund syndrome is characterized by a painful soft tissue swelling at the Achilles tendon insertion, that is, the point of attachment of the tendon to the bone of the heel. In many cases, a bony deposit may develop on the back of the heel. A possible additional symptom of Haglund syndrome is inflammation of the bursa, a fluid-filled sac that decreases friction between the Achilles tendon and the heel, a condition known as retrocalcaneal bursitis. The Achilles tendon itself may also thicken and the soft tissue overlying the tendon may actually bulge.

It is believed that Haglund's syndrome results from the repetitive application of trauma or stress to the heel. Certain stiff, low-backed shoes, such as low-top tennis shoes, may contribute to the problem in particular individuals.

Common treatments for Haglund syndrome include the use of heel lifts (foam pads of approximately 0.25 inches in thickness), oral pain relievers and various physical therapy treatments and flexibility exercises. Surgical procedures may also be utilized in more severe cases. These surgical procedures include: the diagonal removal of heel bone known as oblique calcaneal osteotomy; removal of the deep and superficial retrocalcaneal bursae; and cleaning and tendon repair.

Achilles tendonitis is responsible for about 20% of the foot and ankle problems suffered by runners. There appear to be two types of Achilles tendonitis. One affects the tendon where it connects to the heel bone. The other affects the musculotendonous junction. The affliction is characterized by soft tissue swelling, tenderness to the touch and roughening about the tendon known as crepitus. There is also pain with active pointing and passive raising of the foot.

A number of problems are believed to cause Achilles tendonitis. These include the application of abnormal mechanical longitudinal stress on the tendon, poor flexibility and overuse and/or overload.

Common treatments for Achilles tendonitis include rest, the use of heel lifts or shoe inserts, anti-inflammatory medications as well as various physical therapy treatments and exercises.

Sever's disease was first described in 1912 as resulting from a sclerosis or thickening and irregularity of the growth plate known as the calcaneal apophysis. Presently, it is believed the condition results from inflammation of the soft tissues of the heel following an injury. Sever's disease may result in a number of conditions including retrocalcaneal bursitis (described above), traction apophysitis (i.e. pulling of tendon away from bone) and osteochondrosis of the calcaneal apophysis (irritation and inflammation of bone and cartilage in the heel).

The condition is fairly common in boys from 8–15 years of age. It is characterized by pain down the back of the heel, pain with either passive raising of the foot or a rapid, repetitive pointing of the foot, and a spring gait. Running and jumping aggravate the condition.

Common treatments for Sever's disease include rest, various physical therapy treatments (excluding ultrasound), flexibility exercises and heel lifts.

With any of these ailments, the utilization of more conservative treatment methods is preferred. Thus, heel lifts, rest and specific exercises to increase flexibility are often prescribed. While these methods and techniques are effective for many individuals, they are ineffective for a significant number of others for a number of reasons.

While heel lifts relieve pain symptoms by raising the heel and shortening the length of the Achilles tendon, they do not fully address the causative factors of the ailments. Thus, successful treatment with heel lifts usually requires sufficient rest. Many physically active people suffering from, for example, Achilles tendonitis simply do not allow for the necessary rest. Others simply find the heel lifts inconvenient and uncomfortable and do not use them as prescribed. Thus, recovery is slowed. A need is, therefore, identified for an improved and more efficient, conservative treatment for the causes of posterior heel pain.

BRIEF SUMMARY OF THE INVENTION

Accordingly, it is a primary object of the present invention to provide a prosthetic device for treating and relieving posterior heel pain overcoming the above-described limitations and disadvantages of the prior art.

Another object of the present invention is to provide a lightweight brace for treating posterior heel pain that is both convenient to use and comfortable to wear.

An additional object of the present invention is the provision of a versatile brace that made be utilized to effectively treat Haglund syndrome, Achilles tendonitis, and Sever's disease.

Still another object of the present invention is to provide a brace for the effective treatment of posterior heel pain that also advantageously allows the individual to proceed with his or her activities in a substantially normal fashion.

Yet another object of the present invention is to provide a brace that not only alleviates posterior heel pain, but also addresses the causative factors of the disorder whether it results from Haglund syndrome, Achilles tendonitis or Sever's disease.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved brace is provided for treating inflamed tissue and relieving the posterior heel pain of a patient. The brace includes a means or member for mounting the brace about the heel and foot of the patient. Preferably, the mounting member includes a foot receiving sleeve that is connected to an upper body portion that engages the ankle. A fastener is provided for releasably securing the upper body portion of the brace to the ankle. For maximum effectiveness, the brace fastener is infinitely adjustable. Such a fastener may be of the hook and loop variety as is available under the trademark VELCRO.

Preferably, a heel receiving opening is provided in the brace between the foot receiving sleeve and the upper body portion that engages the ankle. In addition, an opening is provided in the mounting member across the front face of the ankle. Together, the heel and ankle face openings serve to allow full freedom of movement to the ankle while also minimizing movement of the brace relative to the ankle when flexing and extending the ankle. Thus, the brace is always maintained in proper position.

A treatment pad is fastened to the rear of the upper body portion of the mounting member above the heel opening. Preferably, the treatment pad is substantially U-shaped and formed of foam rubber so as to provide both cushioning and support to the Achilles tendon area of the patient.

Additionally, means are provided for selectively fastening the treatment pad to the mounting member. Thus, the pad may be mounted in a first position around the posterior protrusion on the calcaneous or heel bone of the patient so as to be adapted to directly cushion and reduce pressure placed on the inflamed tissue of the heel. More specifically, the arms of the U-shaped pad may be placed in a straddling relationship to the Achilles tendon and subcutaneous bursa of the patient with the base portion that joins the arms extending across the lower margin of the subcutaneous bursa. Posterior heel pain resulting from Haglund syndrome or Sever's disease may be effectively treated and relieved when the pad is positioned in this manner.

Conversely, where posterior heel pain is the result of Achilles tendonitis, the treatment pad may be inverted. When inverted, the arms of the pad again are in straddling relationship to the Achilles tendon. The base portion, however, extends above the arms and across the Achilles tendon above the inflamed tissue. By tightening the strap of the brace-mounting member, selective positive pressure may be placed across the Achilles tendon at the base portion of the pad. This positive pressure produces a counterforce on the tendon that serves to reduce longitudinal stress. Further, the cushioning effect of the pad serves to relieve pain. Thus, the device of the present invention effectively serves to both alleviate the symptoms as well as address the cause of the ailment. Further, this is achieved even if the patient continues to proceed with his or her normal activities.

Still other objects of the present invention will become readily apparent to those skilled in this art from the following description wherein there is shown and described a preferred embodiment of this invention, simply by way of illustration of one of the modes best suited to carry out the invention. As will be realized, the invention is capable of other differing embodiments, and its several details are capable of modifications in various, obvious aspects, all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention, and together with the description serves to explain the principles of the invention. In the drawing:

FIG. 1 is a side elevational view of the brace of the present invention shown over the foot, ankle and heel of a patient;

FIG. 2 is a perspective view showing the brace of the present invention with the ankle fastening strap opened and the treatment pad positioned for treating, for example, Haglund syndrome and Sever's disease;

FIG. 3 is a perspective view of the present invention similar to FIG. 2 showing the manner in which the treatment pad may be positioned and attached to the mounting member of the brace;

FIG. 4 is a perspective view showing the fastening hook structure that is provided on one face of the treatment pad;

Figure 5:
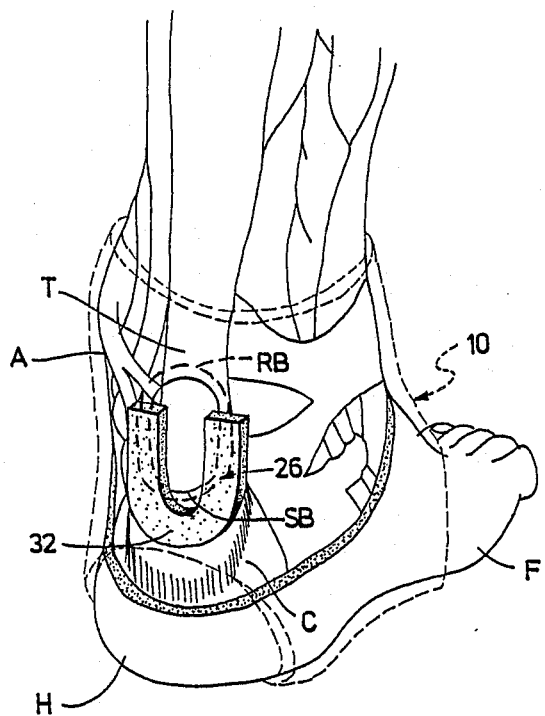
FIG. 5 is a rear perspective view showing the positioning of the treatment pad when treating Haglund syndrome or Sever's disease.

Reference will now be made in detail to the present preferred embodiment of the invention, an example of which is illustrated in the accompanying drawing.

DETAILED DESCRIPTION OF THE INVENTION

Reference is now made to the drawing figures showing the ankle brace 10 of the present invention. The brace 10 is particularly effective in treating inflamed tissue and relieving the posterior heel pain of a patient. The brace 10 is designed so as to be adapted for use in treating either the left or right heel. Further, as described below, the brace 10 is effective in treating a number of different causes of posterior heel pain. As such, the brace 10 is substantially "all purpose" for this type of injury.

As shown in FIG. 1, the brace 10 includes a member 12 for mounting the brace over the heel H and across the ankle A of the patient. Preferably, the member 12 is constructed from a resilient and elastic material such as neoprene. The thickness of the neoprene may range between approximately 0.0625 and 0.25 inches as desired.

The member 12 includes a sleeve 14 designed to receive and fit snugly around the foot F. The sleeve 14 is connected by two flaps or margins 16 of material to an upper body portion 18. A heel receiving opening 20 is outlined and defined between the sleeve 14, margins 16 and upper body portion 18. The opening 20 is substantially circular in shape. In addition, an opening 22 is provided across the front face of the ankle. The end margins of the opening 22 are stitched together as shown at 23 so that the member 12 fully conforms to the heel and ankle. Together, the openings 20 and 22 serve to minimize movement of the brace 10 relative to the heel H and ankle A when flexing and extending the ankle. Further, they allow full freedom of movement to the ankle.

An adjustable fastener 24 including a strap 25 is provided for releasably securing the upper body portion 18 of the brace 10 around the ankle A. The fastener 24 may be a hook and loop fastener such as available under the trademark VELCRO and shown in drawing FIGS. 2 and 3. Of course, other types of fasteners may also be utilized.

A treatment pad 26 is fastened to the interior face of the upper body portion 18 above the heel opening 20. The pad 26 is preferably U-shaped and formed of foam rubber (such as sold under the trademark PPT) so as to cushion and support the Achilles tendon area as described in greater detail below. The pad 26 may have a thickness between approximately 0.1275 and 0.25 inches depending on the desired amount of cushioning to be provided to the Achilles tendon.

As shown in FIG. 3, the pad 26 is fastened to the upper body portion 18 by means of a fastener such as a hook and loop fastener (eg. VELCRO). More specifically, a patch of loop material 28 may be sewn or adhered to the upper body portion 18. A cooperating hook material 29 may be sewn or adhered to one face of the treatment pad 26. As explained in more detail below, the pad 26 may be selectively positioned either to cushion and reduce pressure on the inflamed tissue of the heel or so as to extend across the Achilles tendon of the patient and provide a counterforce to the tendon that reduces longitudinal stress.

When treating heel pain caused by either Haglund syndrome or Sever's disease, it is desired to cushion and reduce pressure on the inflamed tissue. This can be accomplished by positioning the pad 26 on the upper body portion 18 as shown in FIG. 2 (and orientation N in FIG. 3). With the pad 26 in this position and the brace 10 properly positioned over the heel and ankle as shown in FIGS. 1 and 5, the substantially parallel arms 30 of the pad are in a straddling relationship to the Achilles tendon T and subcutaneous bursa SB. The arcuate base portion 32 that joins the arms 30 extends across the lower margin of the subcutaneous bursa SB. Stated another way, the pad 26 is held in engagement across the back of the heel H around the posterior protrusion of the calcaneous or heel bone C of the patient. Thus, the pad partially encircles the inflamed tissue in the area of the subcutaneous bursa SB where the pain is usually concentrated. As such, the pad 26 serves, for example, to engage the top of a shoe back and protect the inflamed tissue from painful contact. This type of direct protection for the inflamed tissue is simply not provided in the prior art by a heel lift which is placed under the heel within a shoe and only serves to shorten the length of the Achilles tendon T.

With the pad 26 in this position, the brace 10 advantageously serves to relieve compressive forces and reduce the pressure placed on the inflamed tissue of the lower heel region including the retrocalcaneal bursa RB and subcutaneous bursa SB. Thus, the cause of the affliction is addressed. In addition, the cushioning action provided by the pad 26 serve to relieve the symptoms of pain. Further, these benefits are provided in such a way so as to allow the individual receiving treatment to remain active.

Figure 6:
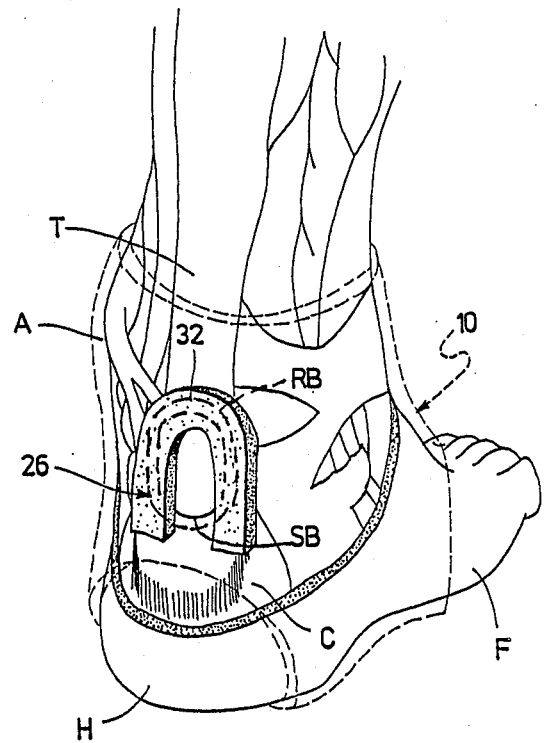
FIG. 6 is a rear perspective view showing the positioning of the treatment pad when treating Achilles tendonitis.

When treating heel pain caused by Achilles tendonitis, it is desired to provide a counterforce to the tendon T that reduces longitudinal stress. This can be accomplished by positioning the pad 26 on the upper body 18 in a fully inverted position to that shown in FIG. 2 (see orientation I in FIG. 3). As best shown in FIG. 6, with the pad 26 in this position and the brace 10 properly positioned over the heel H and ankle A, the substantially parallel arms 30 of the pad are extending downwardly in straddling relationship to the Achilles tendon T. The base portion 32 extends above the arms 30 and across the Achilles tendon above the inflamed tissue of the subcutaneous bursa SB. By adjusting the fastening strap 25 across the ankle A, the counterforce provided to the Achilles tendon can be varied. For example, tightening the strap 25 firmly across the ankle A serves to increase the counterforce provided at the point where the base portion 32 of the pad 26 extends across the Achilles tendon T. That point lies approximately along the lower margin of the retrocalcaneal bursa RB and the lower margin of the subcutaneous bursa SB. This counterforce serves to relieve longitudinal stress on the Achilles tendon T.

Advantageously, by relieving the longitudinal stress on the tendon, the underlying cause of Achilles tendonitis is addressed and even controlled. Further, the pad 26 of brace 10 also serves to cushion the inflamed tissue from compression forces so as to reduce heel pain. Once again, these benefits are provided in such a way so as to allow the individual receiving treatment to remain active.

In summary, numerous benefits result from employing the concepts of the present invention. The brace 10 effectively relieves a number of causes of posterior heel pain including Haglund syndrome, Achilles tendonitis, and Sever's disease. Advantageously, the brace is constructed from lightweight material and may be comfortably worn by the patient over extended periods of time. Further, the brace is convenient to use. In addition, the treatment pad 26 may be selectively positioned so as to either reduce the pressure placed on the inflamed tissue or provide a counterforce to the tendon that reduces longitudinal stress. Thus, it should be appreciated that the brace provides the doctor and patient with outstanding versatility in a single device. Further, the brace not only alleviates posterior heel pain but also effectively addresses the causative factors of the pain. Consequently, treatment time is reduced. In addition, all these benefits are provided even as the patient remains active.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. A brace, said brace including means for treating inflamed tissue and relieving posterior heel pain of a patient, comprising:
means for mounting said brace about the heel of the patient;
a treatment pad; and
means for selectively fastening said treatment pad to said mounting means so that said pad is in one of two positions, said positions consisting of a first position in which said pad is positioned around the posterior protrusion on the calcaneous of the patient to cushion and reduce pressure placed on the inflamed tissue, and a second position, in which said pad is rotated relative to said first position, and extends across the Achilles tendon of the patient above the inflamed tissue to provide a counter force to the tendon that reduces longitudinal stress.

2. The brace set forth in claim 1, wherein said treatment pad is substantially U-shaped including two substantially parallel arms and an arcuate base portion joining the arms.

3. The brace set forth in claim 2, wherein said arms of said pad are in straddling relationship to the bursa of the patient with said base portion extending across the lower margin of said bursa when in said first position.

4. The brace set forth in claim 2, wherein said arms of said pad are in straddling relationship to said Achilles tendon with said base portion extending above said arms and across said Achilles tendon above the inflamed tissue when in said second position.

5. The brace set forth in claim 1, wherein said mounting means includes a foot receiving sleeve connected to an upper body portion for engaging the ankle.

6. The brace set forth in claim 5, wherein said upper body portion includes means for releasably securing said brace to the ankle.

7. The brace set forth in claim 6, wherein said securing means is an infinitely adjustable hook and loop fastener.

8. The brace set forth in claim 1, wherein said mounting means includes a heel receiving opening and an ankle face opening that allow full freedom of ankle movement while minimizing movement of the brace relative to the ankle when flexing and extending the ankle.

9. The brace set forth in claim 8, wherein said heel receiving opening is substantially circular in shape.

10. The brace set forth in claim 1, wherein said treatment pad fastening means is a hook and loop fastener.

11. The brace set forth in claim 1, wherein said treatment pad is constructed of foam rubber having a thickness between substantially 0.1275 and 0.25 inch.

12. The brace set forth in claim 5, wherein said foot receiving sleeve and upper body portion are constructed of neoprene having a thickness between substantially 0.0625 and 0.25 inches.

* * * * *